United States Patent

Mueller et al.

[11] Patent Number: 5,336,836
[45] Date of Patent: Aug. 9, 1994

[54] REMOVAL OF ACETALDEHYDE FROM HYDROCARBONS

[75] Inventors: Ulrich Mueller, Neustadt; Ralf Weiss, Ludwigshafen; Klaus Diehl, Hassloch; Gerhard Sandrock, Frankenthal; Lothar Sauvage, Ludwigshafen, all of Fed. Rep. of Germany

[73] Assignee: BASF Aktiengesellschaft, Ludwigshafen, Fed. Rep. of Germany

[21] Appl. No.: 98,730

[22] Filed: Jul. 29, 1993

[30] Foreign Application Priority Data

Aug. 8, 1992 [DE] Fed. Rep. of Germany ....... 4226302

[51] Int. Cl.$^5$ ............................................. C07C 7/12
[52] U.S. Cl. .................................. 585/824; 585/820
[58] Field of Search .............................. 585/824, 820

[56] References Cited

U.S. PATENT DOCUMENTS

| | | | |
|---|---|---|---|
| 2,825,721 | 3/1958 | Hogan et al. | 260/88.1 |
| 2,930,789 | 3/1960 | Kerber et al. | 260/94.9 |
| 2,945,015 | 7/1960 | Detter | 260/88.2 |
| 3,663,641 | 5/1972 | Hanson | 260/681.5 |
| 4,391,971 | 7/1983 | Massey et al. | 528/481 |

FOREIGN PATENT DOCUMENTS

| | | |
|---|---|---|
| 075421 | 3/1983 | European Pat. Off. . |
| 1011624 | 4/1983 | U.S.S.R. . |

OTHER PUBLICATIONS

J. Chem. Soc. Faraday Trans, 1990 86(1), 205–210, The Adsorption of Ethanal by Some Type A Zeolites, Howard et al.

Chem. Abstract SU 1011-624-A (page & date unavailable).

*Primary Examiner*—Anthony McFarlane
*Assistant Examiner*—Nhat D. Phan
*Attorney, Agent, or Firm*—Keil & Weinkauf

[57] ABSTRACT

Acetaldehyde is removed from $C_3$–$C_{15}$ hydrocarbons by contacting the hydrocarbon or a hydrocarbon mixture in liquid phase with a zeolite whose pores have a width which is greater than 0.3 nm and up to 0.75 nm.

7 Claims, No Drawings

REMOVAL OF ACETALDEHYDE FROM HYDROCARBONS

The present invention relates to a process for removing acetaldehyde from $C_3$–$C_{15}$ hydrocarbons.

The thermal or thermal/catalytic cracking of natural gas, refinery gas or certain petroleum fractions, as is carried out, for example, in steam crackers, results, after workup of the products, in, among other things, mixtures of butadiene, butanes, 1- and 2-butenes and isobutene, which are generally called $C_4$ cuts (Weissermel, Arpe, Industrielle Organische Chemie, Verlag Chemie 1988, p. 68).

These $C_4$ cuts contain traces of acetaldehyde. Extraction of butadiene from the $C_4$ cut also removes acetaldehyde from the remaining hydrocarbons, called the raffinate. If, however, the $C_4$ cut is further processed by, for example, selective hydrogenation of butadiene to butene, the acetaldehyde is not removed. Acetaldehyde is in principle unwanted in hydrocarbons, being capable, among other things, of inactivating the catalysts used in the further processing of $C_4$ cuts.

SU-A 1011624 discloses a process for removing carbonyl impurities from gaseous isobutene streams by adsorption onto a magnesium A zeolite (Mg A zeolite).

The adsorption of pure gaseous acetaldehyde onto a sodium A zeolite is described in J. Chem. Soc. Faraday Trans. 86 (1990) 205 in connection with infrared investigations.

It is an object of the present invention to provide a process which separates acetaldehyde from hydrocarbons with maximum selectivity and economy.

We have found that this object is achieved by a process for removing acetaldehyde from $C_3$–$C_4$ hydrocarbons, which comprises contacting the hydrocarbon or a hydrocarbon mixture in liquid phase with a zeolite whose pores have a width which is greater than 0.3 nm and up to 0.75 nm.

The acetaldehyde is adsorbed onto zeolites. Zeolites are also called molecular sieves and are crystalline aluminosilicates which have a highly ordered structure with a rigid three-dimensional network of $SiO_4$ and $AlO_4$ tetrahedra which are linked by shared oxygen atoms. The charge on the aluminum-containing tetrahedra is balanced by inclusion of cations in the crystal, e.g. alkali metal or hydrogen ions. Cation exchange is possible. The zeolites may also contain in place of aluminum in the lattice other elements such as B, Ga, Fe, Cr, V, As, Sb, Bi or Be or mixtures thereof, and the silicon may also be replaced by another tetravalent element such as Ge, Ti, Zr or Hr.

Suitable zeolites for the process according to the invention have pores with a width which is greater than 0.3 and up to 0.75 nm. This width is determined by the crystal structure and can be determined, for example, from X-ray data. The diffusion of acetaldehyde into zeolites with smaller pores is, because of its size, only poor, and thus it cannot be satisfactorily adsorbed. Zeolites of the A, L, X and Y types are preferred, and those of the A and X types are particularly preferred. Sodium zeolites are very particularly preferred.

Na A zeolites with pores 0.4 nm wide are particularly suitable for removing acetaldehyde from mixtures of propene, butane, 2-butene and butadiene. If the acetaldehyde is mixed only with branched hydrocarbons such as isobutane or isobutene, it is particularly advantageous to use an Na A zeolite or to replace the Na A zeolite partly or entirely by alkaline earth metal A zeolites such as Ca A zeolites.

The zeolites are prepared by conventional methods (eg. Ullmanns Encyclopädie d. Techn. Chemie, 4th edition, Vol. 17, (1983) pp. 9–17). The zeolites can, after removal of trapped water by calcining, be shaped to strands or tablets with binders. Suitable binders are aluminas, silica, mixtures of highly disperse $SiO_2$ with $Al_2O_3$, $TiO_2$, $ZrO_2$ or clay.

The process according to the invention makes it possible to remove acetaldehyde from hydrocarbons which have from 3 to 15 carbon atoms. Smaller hydrocarbons are so similar in size to acetaldehyde that they compete for adsorption in the zeolite. The hydrocarbons comprise alkanes such as propane, n-butane, isobutane, n-pentane, 2-methylbutane, 3-methylbutane, alkenes such as propene, 1-butene, 2-butene, 1-pentene, cyclohexene as well as 1,3-butadiene, alkynes and aromatic compounds such as benzene, toluene, o-xylene, m-xylene and p-xylene. The process is particularly important for treating $C_4$ cuts, from which butadiene can have already been removed, and for isobutene.

The process according to the invention is particularly advantageous for removing acetaldehyde in amounts of from 10 to 500 ppm, as are present in $C_4$ cuts, for example. However, it is also able to reduce higher acetaldehyde concentrations in the range up to 50,000 ppm (5% by weight).

The process according to the invention is, as a rule, carried out at from −10 to 60° C., preferably from 15 to 35° C. Lower temperatures are too costly for large streams, while at higher temperatures the adsorption capacity of the zeolites decreases markedly.

The pressure is chosen so that the hydrocarbons to be purified are liquid. The pressure is generally from 1 to 70, preferably from 5 to 35, bar. It is advantageous to use the pressure under which the hydrocarbon is liquid on production, e.g. by petroleum cracking.

It has proven advantageous in the treatment of large product streams to employ the zeolite in the form of a fixed bed in an adsorption column, through which the hydrocarbon is passed. The hydrocarbon to be treated is passed through the column in an ascending or descending manner. The height of the bed is preferably from 2 to 15 times the diameter of the bed. It is recommended that the linear velocity of the liquid cross-section, calculated from the ratio of the volume flow to the cross-section of the adsorber bed, is from 0.5 to 35 cm/min, preferably from 1 to 15 cm/min and, in particular, from 1.5 to 10 cm/min.

Once the zeolite is saturated it can be regenerated by passing over an inert gas such as nitrogen under atmospheric pressure and at from 150 to 250° C, which takes about 4–12 hours.

For continuous operation, it is expedient to provide two adsorption columns, one for adsorption and the other for desorption (regeneration). It is also possible for a plurality of adsorption columns to be arranged in parallel on this principle.

The process according to the invention makes it possible to remove acetaldehyde from $C_3$–$C_4$ hydrocarbons down to a residual content of less than 1 ppm. Such a content does not, as a rule, interfere with the use the further processing of the hydrocarbons. The zeolite used for this purpose is easy to regenerate. Furthermore, traces of water can also be removed from the hydrocarbons by adsorption.

EXAMPLES

Hydrocarbons with particular acetaldehyde concentrations were passed over zeolites. The acetaldehyde concentration was measured at various times after adsorption. Details are to be found in the following Table.

TABLE

| Example | Zeolite | Pore width [nm] | Amount of zeolite [kg] | Bed length/ diameter | Hydrocarbon |
| --- | --- | --- | --- | --- | --- |
| 1 | Na A | 0.4 | 196 | 3.6 | 8.6% by weight n-butane |
|   |      |     |     |     | 4.1% by weight isobutane |
|   |      |     |     |     | 26.0% by weight isobutene |
|   |      |     |     |     | 33.0% by weight 1-butene |
|   |      |     |     |     | 28.3% by weight 2-butene |
| 2 | Na A | 0.4 | 521 | 5 | 8.6% by weight n-butane |
|   |      |     |     |   | 4.1% by weight isobutane |
|   |      |     |     |   | 26.0% by weight isobutene |
|   |      |     |     |   | 33.0% by weight 1-butene |
|   |      |     |     |   | 28.3% by weight 2-butene |
| 3 | Na A | 0.4 | 0.039 | 14 | 8.6% by weight n-butane |
|   |      |     |       |    | 4.1% by weight isobutane |
|   |      |     |       |    | 26.0% by weight isobutene |
|   |      |     |       |    | 33.0% by weight 1-butene |
|   |      |     |       |    | 28.3% by weight 2-butene |
| 4 | Ca A | 0.5 | 0.038 | 14 | 8.6% by weight n-butane |
|   |      |     |       |    | 4.1% by weight isobutane |
|   |      |     |       |    | 26.0% by weight isobutene |
|   |      |     |       |    | 33.0% by weight 1-butene |
|   |      |     |       |    | 28.3% by weight 2-butene |
| 5 | Ca X | 0.75 | 0.035 | 14 | 8.6% by weight n-butane |
|   |      |      |       |    | 4.1% by weight isobutane |
|   |      |      |       |    | 26.0% by weight isobutene |
|   |      |      |       |    | 33.0% by weight 1-butene |
|   |      |      |       |    | 28.3% by weight 2-butene |
| 6 | Na A | 0.4 | 52 | 2.5 | isobutene |
| Comparative | K A | 0.3 | 252 | 3.6 | 8.6% by weight n-butane |
|   |      |     |     |     | 4.1% by weight isobutane |
|   |      |     |     |     | 26.0% by weight isobutene |
|   |      |     |     |     | 33.0% by weight 1-butene |
|   |      |     |     |     | 28.3% by weight 2-butene |

| Example | Temperature T [°C.] | Pressure p [bar] | Linear velocity [cm/min] | Acetaldehyde content before adsorption [ppm] | Acetaldehyde content after adsorption [ppm] |
| --- | --- | --- | --- | --- | --- |
| 1 | 25 | 19 | 6.9 | 260 | after 1 h: <1 |
|   |    |    |     |     | after 3 h: 1.3 |
|   |    |    |     |     | after 6.5 h: 4.2 |
| 2 | 27 | 18 | 4.1 | 195 | after 2 h: 1.1 |
|   |    |    |     |     | after 9 h: 0.14 |
|   |    |    |     |     | after 17 h: 0.28 |
| 3 | 35 | 5 | 1.7 | 40,000 | after 3.5 h: <1 |
| 4 | 35 | 5 | 1.7 | 40,000 | after 3.5 h: <1 |
| 5 | 35 | 5 | 1.7 | 40,000 | after 2 h: <1 |
|   |    |   |     |        | after 3 h: <1 |
|   |    |   |     |        | after 3.5 h: 9.1 |
| 6 | 23 | 14 | 2.7 | 270 (water: 47 ppm) | after 255 h: <2 (<5) |
| Comparative | 27 | 18 | 6.9 | 250 | after 0.5 h: 3 |
|   |    |    |     |     | after 3.5 h: 59 |
|   |    |    |     |     | after 12 h: 129 |
|   |    |    |     |     | after 26 h: 164 |

We claim:

1. A process for removing acetaldehyde from $C_3$–$C_{15}$ hydrocarbons, which comprises contacting the $C_3$–$C_{15}$ or a hydrocarbon mixture of $C_3$–$C_{15}$ hydrocarbon in liquid phase with a zeolite whose pores have a width which is greater than 0.3 nm and up to 0.75 nm.

2. A process as defined in claim 1, wherein the zeolite is an A or X zeolite.

3. A process as defined in claim 1, wherein an acetaldehyde-containing mixture of butanes, 1- and 2-butenes and isobutene is contacted with the zeolite.

4. A process as defined in claim 2, wherein an acetaldehyde-containing mixture of butanes, 1- and 2-butenes and isobutene is contacted with the zeolite.

5. A process as defined in claim 1, wherein acetaldehyde-containing isobutene is contacted with the zeolite.

6. A process as defined in claim 2, wherein acetaldehyde-containing isobutene is contacted with the zeolite.

7. A process as defined in claim 1, wherein the zeolite is an Na A zeolite with pores about 0.4 nm wide.

* * * * *

UNITED STATES PATENT AND TRADEMARK OFFICE
CERTIFICATE OF CORRECTION

PATENT NO.: 5,336,836

DATED: August 9, 1994

INVENTOR(S): MUELLER et al.

It is certified that error appears in the above-identified patent and that said Letters Patent is hereby corrected as shown below:

Claim 1, column 3, line 62, "or a hydrocarbon mixture of" should read --hydrocarbon or a mixture of--.

Signed and Sealed this

First Day of November, 1994

Attest:

BRUCE LEHMAN

Attesting Officer

Commissioner of Patents and Trademarks